US010191045B2

(12) United States Patent
Kim

(10) Patent No.: US 10,191,045 B2
(45) Date of Patent: Jan. 29, 2019

(54) SOL COMPOSITION FOR SOL-GEL BIOCHIP TO IMMOBILIZE PROBE ON SUBSTRATE WITHOUT SURFACE TREATMENT AND METHOD AND SCREENING THEREOF

(71) Applicant: So Youn Kim, Seoul (KR)

(72) Inventor: So Youn Kim, Seoul (KR)

(73) Assignee: So Youn Kim, Seoul (KR)

( * ) Notice: Subject to any disclaimer, the term of this patent is extended or adjusted under 35 U.S.C. 154(b) by 0 days.

(21) Appl. No.: 15/065,494

(22) Filed: Mar. 9, 2016

(65) Prior Publication Data

US 2016/0334400 A1    Nov. 17, 2016

Related U.S. Application Data

(62) Division of application No. 12/162,412, filed as application No. PCT/KR2007/000390 on Jan. 23, 2007, now Pat. No. 9,476,876.

(30) Foreign Application Priority Data

Jan. 27, 2006  (KR) ........................ 10-2006-0008926

(51) Int. Cl.
*G01N 33/543*        (2006.01)
*B01J 19/00*         (2006.01)

(52) U.S. Cl.
CPC .... *G01N 33/54393* (2013.01); *B01J 19/0046* (2013.01); *B01J 2219/0061* (2013.01); *B01J 2219/00623* (2013.01); *B01J 2219/00725* (2013.01); *B01J 2219/00756* (2013.01)

(58) Field of Classification Search
None
See application file for complete search history.

(56) References Cited

U.S. PATENT DOCUMENTS

| 6,632,617 B1 | 10/2003 | Bandman et al. |
| 2002/0028506 A1 | 3/2002 | Ho et al. |
| 2005/0053954 A1 | 3/2005 | Brennan et al. |
| 2006/0223167 A1 | 10/2006 | Chaton et al. |

FOREIGN PATENT DOCUMENTS

| JP | 2005-539215 A | 12/2005 |
| WO | WO 2004/024955 A1 | 3/2004 |
| WO | WO 2004/048603 A1 | 6/2004 |
| WO | WO 2004/092250 A1 | 10/2004 |

OTHER PUBLICATIONS

Ahn, J. et al., "Aptamer Microaaray Mediated Capture and Mass Spectrometry Identification of Biomarker in Serum Samples," Journal of Proteome Research, 9, Aug. 31, 2010, pp. 5568-5573.
Choi, S. et al., "Regulation of TM4SF5-Mediated Tumorigenesis Through Induction of Cell Detachment and Death by Tiarellic Acid," Biochimica et Biophysica Acta1783, Apr. 30, 2008, pp. 1632-1641.
Extended European Search Report, EP Patent Application No. EP 07851308.2, May 12, 2010, 11 pages.
Kim, S. et al., "Improved Sensitivity and Physical Properties of Sol-Gel Protein Chips Using Large-Scale Material Screening and Selection," Anal. Chem. 2006, 78, pp. 7392-7396.
Lee, S. et al., "Focal Adhesion and Actin Organization by a Cross-Talk of TM4SF5 with Integrin $\alpha$2 are Regulated by Serum Treatment," Exp. Cell. Res. 312(16), May 18, 2006, pp. 2985-2993.
Lee, S. et al., "Tetraspanin TM4SF5 Mediates Loss of Contact Inhibition Through Epithelial-Mesenchymal Transition in Human Hepatocarcinoma," The Journal of Clinical Investigation, col. 188,No. 4, Apr. 2008, pp. 1354-1366.
Müller-Pillasch, F. et al., "Identification of a New Tumour-Associated Antigen TM4SF5 and its Expression in Human Cancer," Gene 208, 1998, pp. 25-30.
Park, S. et al., "Selection and Elution of Aptamers Using Nanoporous Sol-Gel Arrays with Integrated Microheaters", Lab Chip, 9, Feb. 13, 2009, pp. 1206-1212.
Dave, B. et al., "Sol-Gel Encapsulation Methods for Biosensors", Anal. Chem., Nov. 15, 1994, p. 1120-1127, vol. 66, No. 22.
Edminston, P. et al., "Spectroscopic Characterization of Albumin and Myoglobin Entrapped Bulk Sol-Gel Glasses", J. Coll. Interf. Sci., 1994, pp. 395-406, vol. 163.
Gill, I. et al., "Bioencapsulation within synthetic polymers (Part 1): sol-gel encapsulated biologicals", TIBTECH, Jul. 2000, p. 282-296, vol. 18.
Kim, E. et al., "Polymer microstructures formed by moulding in capillaries", Nature, Aug. 17, 1995, p. 581-584, vol. 376, No. 17.
Kim, Y. et al., "Stable Sol-Gel Microstructured and Microfluidic Networks for Protein Patterning", Biotechnol. Bioeng., 2001, pp. 331-337, vol. 73.
MacBeath, G. et al., Printing Proteins as Microarrays for High-Throughput Function Determination, Science, Sep. 8, 2000, p. 1760-1763, vol. 28.
Marzolin, C. et al., "Communications", Advanced Materials, 1998, pp. 571-574, vol. 10, No. 8.
PCT International Search Report and Written Opinion, PCT Application No. PCT/KR2007/000390, dated Apr. 25, 2007, six pages.
Reetz, M. et al., "Entrapment of Biocatalysts in Hydrophobic Sol-Gel Materials for Use in Organic Chemistry", Adv. Mater., 1997, p. 943-954, vol. 9, No. 12.

(Continued)

*Primary Examiner* — Christopher M Gross
(74) *Attorney, Agent, or Firm* — Fenwick & West LLP

(57) ABSTRACT

The present invention relates to a method for screening a sol composition for sol-gel biochips, which is used to immobilize a probe on a surface-untreated substrate, also relates to a sol composition screened by said method and a sol-gel biochip comprising said sol composition immobilized thereon. The sol composition screened by the disclosed method can be mixed with a probe, and the sol mixture can be integrated on 96-well plates, which are widely used in existing bioassays, without surface treatment. Also, the biochip can provide a sensitive and specific good analysis results because this immobilization methods of probe maintain the nature of probes without modification.

9 Claims, 6 Drawing Sheets

(56) References Cited

OTHER PUBLICATIONS

Schuller, O. et al., "Fabrication of photonic crystal lasers by nanomolding of solgel glasses", Applied Optics, Sep. 20, 1999, p. 5799-5802, vol. 38, No. 27.

Xu, Q. et al., "Protein and Chemical Microarrays—Powerful Tools for Proteomics," Journal of Biomedicine and Biotechnology, 2003:5, pp. 257-266.

Ahn, J., et al., "Sol-gel Material Optimization for Aptamer Biosensors," Molecular & Cellular Toxicology, 2008, vol. 4, No. 2, pp. 100-105.

Ahn, J-Y., et al., "A Sol-Gel-Based Microfluidics System Enhances the Efficiency of RNA Aptamer Selection," Ahn, J.Y., et al., Oligonucleotides, 2011, vol. 21, No. 2, pp. 93-100.

Ahn, J.Y., "Sol-Gel Derived Nanoporous Compositions for Entrapping Small Molecules and Their Outlook toward Aptamer Screening," Analytical Chemistry. 2012. 84(6): p. 2647-2653.

Bae, H., et al., "Sol-Gel SELEX Circumventing Chemical Conjugation of Low Molecular Weight Metabolites Discovers Aptamers Selective to Xanthine," Nucleic Acid Ther. 2013. 23(6): p. 443-9.

Kim, S., et al., "Improved Sensitivity and Physical Properties of Sol-Gel Protein Chips Using Large-Scale Material Screening and Selection," Anal Chem. 2006, vol. 78, No. 21, pp. 7392-7396.

Kwon, J., et al., "High Diagnostic Accuracy of Antigen Microarray for Sensitive Detection of Hepatitis C Virus Infection," Clinical Chemistry, 2008, vol. 54, No. 2, pp. 424-428.

Lee, K., et al., "Serologic Markers of Viral Hepatitis of Korea University Medical Center Patients," Korean J Lab Med., 2005, vol. 25, No. 1, pp. 61-65 (With English Abstract).

Lee, S., "Improved porous silicon microarray based prostate specific antigen immunoassay by optimized surface density of the capture antibody," AnalyticaChimicaActa., 2013, vol. 796, pp. 108-114.

Lee, S.W., et al., "A Sol-Gel-Integrated Protein Array System for Affinity Analysis of Aptamer-Target Protein Interaction," Nucleic Acid Therapeutic, 2011, vol. 21, No. 3, pp. 179-183.

Lee, S., et al., "Chip-based detection of Hepatitis C virus using RNA aptamers that specifically bind to HCV core antigen," BiochemBiophys Res Commun. 2007, 358(1), 47-52.

Lee, S., et al., "Improvement of Protein Chip Sensitivity by Increasing Salt concentration," Biochip Journal. 2007, 1(2), 107-10.

Park, S.-M., et al., "Selection and elution of aptamers using nanoporous sol-gel arrays with integrated microheaters," Lab on a Chip, 2009, vol. 9, No. 9, pp. 1206-1212.

Ren, S., et al., "Trends in Three-dimensional Biochips," Biochip Journal. 2008, 2(3), 155-9.

Wang, Z-W., et al., "In Vitro selection and identification of ssDNA aptamers recognizing the Ras protein," Molecuar Medine Reports, 2014, vol. 10, pp. 1481-1488.

Ren, S., et al., "In vitro selection of ssDNA aptamers for detection of nonylphenol using sol-gel microfluidic chips," Molecular & Cellular Toxicology. 2009. p. 86-86. (Abstract).

1 : Negative
2 : core 100ng
3 : Positive(a-R-cy3 1/100)

SOL COMPOSITION FOR SOL-GEL BIOCHIP TO IMMOBILIZE PROBE ON SUBSTRATE WITHOUT SURFACE TREATMENT AND METHOD AND SCREENING THEREOF

This application is a divisional of U.S. application Ser. No. 12/162,412 filed on Apr. 24, 2009, now U.S. Pat. No. 9,476,876; which is a 371 national-stage application of PCT/KR2007/000390, filed Jan. 23, 2007, which claims priority to KR Provisional Application 10-2006-0008926, filed Jan. 27, 2006. The entire contents of each of these applications are hereby incorporated by reference.

TECHNICAL FIELD

The present invention relates to a method for screening a sol composition for sol-gel biochips, which is used to immobilize a probe on a surface-untreated substrate, a sol composition screened by said method, and a sol-gel biochip comprising said sol composition immobilized thereon.

BACKGROUND ART

The biochip is a representative example of novel technology combining material technology such as nanotechnology (NT), biotechnology (BT) which is contents and applied field of the material technology and information technology (IT) to analyze a large amount of results. The biochip is formed by high-density micro-arraying of various kinds of biomaterials on a unit area of a surface of a solid support. The biochip technologies include a technology to immobilize biomaterials, a technology to make the chip surface biocompatible, microarray technology of biomaterials, an assay technology to perform various biological reactions on a produced chip, a technology to detect reaction results, a protein engineering to produce biomaterials to be immobilized and genetic recombination technology.

A protein chip representative of the biochips is formed by intensive micro-arraying of various proteins on a unit area of the surface of a solid support. By using the protein chip, it is possible to conduct an experiment for multiple purposes, such as diagnosis of diseases, high throughput screening (HTS), enzyme activity test and the like, with a small amount of samples.

There have been attempts to produce the protein chip by employing the same principles and technical factors as in the production of DNA chips, which have been already developed and commonly used. Generally, most of the commonly used DNA chips are produced by immobilizing DNA on a glass substrate, the surface of which has been pretreated with a coating material. When the protein chip is fabricated according to a method similar to that used in the production of DNA chips, that is, when the protein chip is fabricated by immobilizing proteins on a glass substrate whose surface has been pretreated with a coating material, various problems are likely to occur due to the difference in physical and chemical properties between the target proteins to be immobilized.

Previous protein chip was produced by immobilizing proteins on a surface-treated glass substrate and used to perform a simple binding assay. The performance of the protein chip was determined by the activity of the immobilized protein and it was hard to work successfully (MacBeath and Schreiber, Science 289:1760, 2000). Such problems are caused by the denaturation, inactivation and degradation of proteins resulting from the difference in the inherent physical and chemical properties of proteins.

In order to solve these problems, researches and studies have been conducted on surface treatment technology for immobilizing proteins suitable for protein characteristics which are distinguished from those of DNA and on materials for immobilizing protein. Such research and studies are focused on a method for performing immobilization on the surface of a protein chip while maintaining the activity of the protein. Examples thereof include a hydrogel-coated slide (PerkinElmer), Versalinx chip (Prolinx), PDC chip which is a biochip commercially available from Zyomyx, etc.

In particular, the hydrogel-coated slide is a technology using a 3-dimensional polyacrylamide gel, in which a Swiss glass with an optically level, silane treated surface is used as a base material and a surface-modified acrylamide polymer is applied thereon to improve the binding force and structural stability of a protein. Herein, the protein is immobilized by a covalent bond with a functional group of polyacrylamide gel. Also, the Versalinx chip of Prolinx comprises a self-assembly monolayer of biotin-conjugated poly(L-lysine)-g-poly(ethylene glycol) formed on a $TiO_3$, in which a protein is immobilized on the self-assembly monolayered surface, whereby the activity of the protein can be improved. These methods form a 3-dimensional micro-structure and covalently immobilize proteins on a modified surface so as to maintain the activities of proteins within spots. In addition to these methods, it is also possible to make micro-well type of chips through microprocessing so as to produce solution-state chips.

Meanwhile, a sol-gel process is a technology which has been used to make a micro-structure by microprocessing, and in particular, it is a technology comprised of forming a binding net by a mild process and immobilizing biomolecules within the binding net by methods other than a covalent bond, instead of chemically attaching biomolecules to an inorganic material (Gill, I. and Ballesteros, A., *Trends Biotechnol.*, 18:282, 2000). Biomolecules including enzymes are immobilized on a mass sol-gel matrix for use in the production of biocatalysts or biosensors (Reetz et al., *Adv. Mater.*, 9:943, 1997). Specially, the sol-gel matrix is also used in the detection of optical color development due to its transparency and optical property (Edminston et al., *J. Coll. Interf. Sci.*, 163:395, 1994). Also, biomolecules are known to be not only chemically but also thermally stabilized when they are immobilized on a sol-gel matrix (Dave et al., *Anal. Chem.*, 66:1120, 1994).

In case of the biosensor, the sol-gel reaction is used as a method for patterning by forming a micro structure on a solid support as well as for simple immobilization.

Herein, the patterning method includes shaping a liquid-state sol using a mold by fluid dynamics, gelatinizing the shaped material and separating the mold to form a pattern. For example, a technology designated as micro-moduling in-capillaries (MIMIC) technology is for patterning mesoscopic silica (Kim et al., *J. Ferment. Bioeng.* 82:239, 1995; Marzolin et al., *Adv. Mater.* 10:571, 1998; Schuller et al., *Appl. Optics* 38:5799, 1999). This technology can be used in basic patterning of micro-fluid engineering.

However, since the activity of protein can be affected by various factors such as pH, it is important to set conditions for the maintenance of the activity by adding protein from its sol state in the sol-gel process. For this purpose, technologies for patterning a protein by previously mixing the protein with a sol using various mild conditions such as neutral pH (Kim et al., *Biotechnol. Bioeng.* 73:331 to 337, 2001) are proposed, but there are problems in that the sol-gel process rapidly progresses at neutral pH to form a gel and cracks may occur or the gel turns opaque, according to the choice of additives.

To overcome the above-described problems, the present inventors previously developed a biochip using a sol-gel reaction (Korean Patent Laid-Open Publication No. 10-2004-0024510). Specifically, in the prior art, because there was no technology by which a sol-gel matrix containing biomaterials, including proteins, could be immobilized on a chip substrate in the form of spots, there was no biochip in which a sol-gel matrix having biomaterials immobilized thereon was integrated in the form of spots. In the prior patent, a technology of treating the surface of a chip substrate with a special coating material was developed, and thus a biochip employing a sol-gel reaction on the chip substrate could be prepared for the first time. By the technology of treating the chip substrate surface according to the prior patent, a sol mixture containing biomaterials can be integrated on the chip substrate in the form of spots, a sol-gel reaction for gelling the sol mixture can occur on the chip substrate, and sol-gel matrixes can be immobilized on the chip substrate. In particular, in the prior patent, unlike the prior biochips having biomaterials immobilized on the chip substrate surface by covalent bonds, a biochip comprising biomaterials entrapped and encapsulated in the pores of gel-type spots, which are integrated and immobilized on a chip substrate, was developed.

However, in the case of this biochip, in order to immobilize the biomaterial-containing gel spots on the substrate, the surface of the substrate should be treated with a coating agent such as polyvinyl acetate, and the sol mixture should be spotted on the surface-treated substrate. Thus, this biochip is disadvantageous in terms of cost or mass production and has a limitation in that it cannot be applied to biochips having a surface or shape which cannot be coated.

Accordingly, the present inventors have made many efforts to find a material composition for use in sol-gel encapsulation, which can strongly bind to a substrate which was not subjected to surface treatment essential for the commercial use of biochips. As a result, the present inventors have designed an efficient method for screening a sol composition and found a sol composition, which can strongly bind to a substrate surface and thus can withstand intense washing during the analysis process of biochips and, at the same time, can provide good assay results, thereby completing the present invention.

SUMMARY OF THE INVENTION

Accordingly, it is an object of the present invention to provide a method for screening a sol composition for sol-gel biochips, which is used to immobilize a probe on a surface-untreated substrate.

Another object of the present invention is to provide a sol composition for PMMA substrates or gold substrates or silicon wafer substrates, screened by said method, as well as a sol-gel biochip comprising said sol composition immobilized thereon.

To achieve the above object, the present invention provides a method for screening a sol composition for sol-gel biochips, which is used to immobilize a probe on a surface-untreated substrate, the method comprising the steps of: (a) obtaining a first library of sol compositions wherein at least one silicate monomer selected from the group consisting of tetramethylorthosilicate (TMOS), methyltrimethoxysilane (MTMOS), tetraethylorthosilicate (TEOS), ethyltrimethoxysilane (ETrEOS), trimethoxysilane (TMS), methyltrimethoxysilicate (MTMS) and 3-aminopropyltrimethoxysilicate (3-ATMS), and at least one additive selected from the group consisting of polyglyceryl silicate (PGS), diglyceryl silane (DGS), 3-glycidoxypropyl trimethoxysilane (GPTMOS), (N-triethoxysilylpropyl)-O-polyethylene oxide urethane (PEOU), glycerol and polyethylene glycol (PEG) having a molecular weight of 100-10,000, are mixed with each other in buffer at various ratios; (b) spotting the first library of sol compositions on a surface-untreated target substrate; (c) measuring the adhesion, appearance, transmittance and gelling time of the spots formed in the step (b), and selecting, based on the measurement results, compositions, which do not show the detachment of spots even when they are scratched with a tip after washing, have a spot diameter of 100-800 µm while maintaining a circular shape, show a self-fluorescence lower than background fluorescence, and have a gelling time of 4-48 hours in a tube and a gelling time of 1-4 hours on the spots of the substrate, thereby obtaining a second library of sol compositions; (d) adding a probe to the second library of sol compositions and spotting the probe-containing second library on a surface-untreated substrate; and (e) measuring the immobilization rate of the spots for the probe, and the specificity between the probe and a target substance, and selecting, based on the measurement results, a sol composition wherein the immobilization rate of the probe is at least 70% and the ratio of specific signals/non-specific signals of the probe and the target substance is at least 3.

The present invention also provides a sol composition for sol-gel biochips, which is used to immobilize a probe on a surface-untreated, plasma-treated PMMA substrate, the sol composition comprises: 17.5-25 parts by weight of TMOS; 5-15 parts by weight of MTMS; 2.5-15 parts by weight of GPTMOS; 12.5 parts by weight of 10 mM HCl; 25 parts by weight of distilled water; 11-13 parts by weight of 10 mM sodium phosphate buffer (pH 5.8); and 10-15 parts by weight of a probe solution. The present invention also provides a sol-gel biochip, in which said sol composition is immobilized on a surface-untreated, plasma-treated PMMA substrate.

The present invention also provides a sol composition for sol-gel biochips, which is used to immobilize a probe on a surface-untreated PMMA substrate, the sol composition comprises: 22.5-25 parts by weight of TMOS; 7.5-10 parts by weight of MTMS; 2.5-5 parts by weight of GPTMOS; 12.5 parts by weight of 10 mM HCl; 25 parts by weight of distilled water; 11-13 parts by weight of 10 mM sodium phosphate buffer (pH 5.8); and 10-15 parts by weight of a probe solution. The present invention also provides a sol-gel biochip, in which said sol composition is immobilized on a surface-untreated PMMA substrate.

The present invention also provides a sol composition for sol-gel biochips, which is used to immobilize a probe on a surface-untreated gold substrate, the sol composition comprises: 16.2-18.7 parts by weight of TMOS; 3.7-6.2 parts by weight of MTMS; 13.7-16.2 parts by weight of GPTMOS; 0.01-20 parts by weight of an adhesive; 12.5 parts by weight of 10 mM HCl; 23.7-24.5 parts by weight of distilled water; 11-13 parts by weight of 10 mM sodium phosphate buffer (pH 5.8); and 10-15 parts by weight of a probe solution. The present invention also provides a sol-gel biochip, in which said sol composition is immobilized on a surface-untreated gold substrate.

The present invention also provides a sol composition for sol-gel biochips, which is used to immobilize a probe on a surface-untreated silicon wafer substrate, the sol composition comprises: 5-30 parts by weight of TMOS; 2-35 parts by weight of MTMS; 1-15 parts by weight of GPTMOS; 0.01-20 parts by weight of an adhesive; 12.5 parts by weight of 10 mM HCl; 23.7-24.5 parts by weight of distilled water; 12.5 parts by weight of 10 mM sodium phosphate buffer (pH 5.8); and 12.5 parts by weight of a probe solution. The present invention also provides a sol-gel biochip, in which said sol composition is immobilized on a surface-untreated silicon wafer substrate.

The above and other objects, features and embodiments of the present invention will be more clearly understood from the following detailed description and accompanying claims.

DETAILED DESCRIPTION OF THE INVENTION, AND PREFERRED EMBODIMENTS

Figure 1:
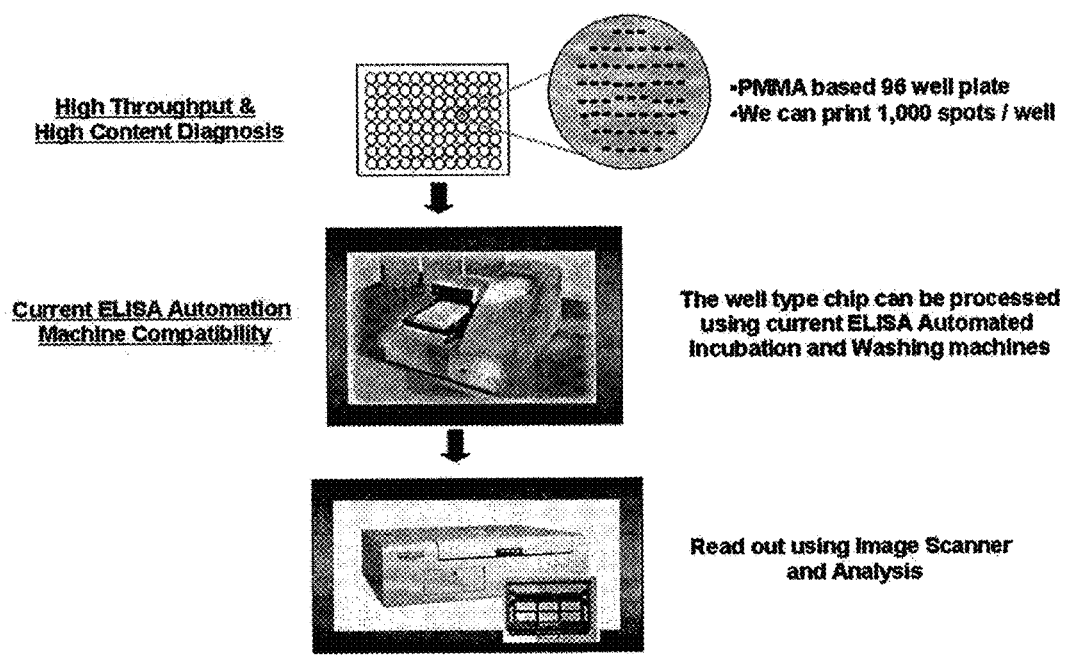
FIG. 1 shows an analysis method that employs a 96-well plate type biochip according to the present invention.

In one aspect, the present invention relates to a method for screening a sol composition for sol-gel biochips, which is used to immobilize a probe on a surface-untreated substrate, the method comprising the steps of: (a) obtaining a first library of sol compositions wherein at least one silicate monomer selected from the group consisting of tetramethylorthosilicate (TMOS), methyltrimethoxysilane (MTMOS), tetraethylorthosilicate (TEOS), ethyltrimethoxysilane (ETrEOS), trimethoxysilane (TMS), methyltrimethoxysilicate (MTMS) and 3-aminopropyltrimethoxysilicate (3-ATMS), and at least one additive selected from the group consisting of polyglyceryl silicate (PGS), diglyceryl silane (DGS), 3-glycidoxypropyl trimethoxysilane (GPTMOS), (N-triethoxysilylpropyl)-O-polyethylene oxide urethane (PEOU), glycerol and polyethylene glycol (PEG) having a molecular weight of 100-10,000, are mixed with each other in buffer at various ratios; (b) spotting the first library of sol compositions on a surface-untreated target substrate; (c) measuring the adhesion, appearance, transmittance and gelling time of the spots formed in the step (b), and selecting, based on the measurement results, compositions, which do not show the detachment of spots even when they are scratched with a tip after washing, have a spot diameter of 100-800 μm while maintaining a circular shape, show a self-fluorescence lower than background fluorescence, and have a gelling time of 4-48 hours in a tube and a gelling time of 1-4 hours on the spots of the substrate, thereby obtaining a second library of sol compositions; (d) adding a probe to the second library of sol compositions and spotting the probe-containing second library on a surface-untreated substrate; and (e) measuring the immobilization rate of the spots for the probe, and the specificity between the probe and a target substance, and selecting, based on the measurement results, a sol composition wherein the immobilization rate of the probe is at least 70% and the ratio of specific signals/non-specific signals of the probe and the target substance is at least 3. In the present invention, the probe is preferably any one selected from the group consisting of proteins, oligopeptides, nucleic acids, low molecular substances, microorganisms, fungi and herbal medicinal materials, and the surface-untreated substrate is preferably any one selected from the group consisting of polymer plates, metals, silicon wafers, glass and LCD.

In another aspect, the present invention relates to a sol composition for sol-gel biochips, which is used to immobilize a probe on a surface-untreated, plasma-treated PMMA substrate, the sol composition comprising the following components, as well as a sol-gel biochip comprising said sol composition immobilized on a surface-untreated, plasma-treated PMMA substrate:

17.5-25 parts by weight of TMOS;
5-15 parts by weight of MTMS;
2.5-15 parts by weight of GPTMOS;
12.5 parts by weight of 10 mM HCl;
25 parts by weight of distilled water;
11-13 parts by weight of 10 mM sodium phosphate buffer (pH 5.8); and
10-15 parts by weight of a probe solution.

In still another aspect, the present invention relates to a sol composition for sol-gel biochips, which is used to immobilize a probe on a surface-untreated PMMA substrate, the sol composition comprising the following components, as well as a sol-gel biochip comprising said sol composition immobilized on a surface-untreated PMMA substrate:

22.5-25 parts by weight of TMOS;
7.5-10 parts by weight of MTMS;
2.5-5 parts by weight of GPTMOS;
12.5 parts by weight of 10 mM HCl;
25 parts by weight of distilled water;
11-13 parts by weight of 10 mM sodium phosphate buffer (pH 5.8); and
10-15 parts by weight of a probe solution.

In the sol composition, said probe is preferably protein, more preferably HCV antigen, and said substrate is preferably 96 well plate.

In yet still another aspect, the present invention relates to a sol composition for sol-gel biochips, which is used to immobilize a probe on a surface-untreated gold substrate, the sol composition comprising the following components, as well as a sol-gel biochip comprising said sol composition immobilized on a surface-untreated gold substrate:

16.2-18.7 parts by weight of TMOS;
3.7-6.2 parts by weight of MTMS;

13.7-16.2 parts by weight of GPTMOS;
0.01-20 parts by weight of an adhesive;
12.5 parts by weight of 10 mM HCl;
23.7-24.5 parts by weight of distilled water;
11-13 parts by weight of 10 mM sodium phosphate buffer (pH 5.8); and
10-15 parts by weight of a probe solution.

In the sol composition, said adhesive is preferably 1010 and/or 1020, and said probe is preferably protein.

In yet still another aspect, the present invention relates to a sol composition for sol-gel biochips, which is used to immobilize a probe on a surface-untreated silicon substrate, the sol composition comprising the following components, as well as a sol-gel biochip comprising said sol composition immobilized on a surface-untreated silicon substrate:

5-30 parts by weight of TMOS;
2-35 parts by weight of MTMS;
1-15 parts by weight of GPTMOS;
0.01-20 parts by weight of an adhesive;
12.5 parts by weight of 10 mM HCl;
23.7-24.5 parts by weight of distilled water;
12.5 parts by weight of 10 mM sodium phosphate buffer (pH 5.8); and
12.5 parts by weight of a probe solution.

As used herein, the term "surface treatment" is the term disclosed in the previous patent (Korean Patent Laid-Open Publication No. 10-2004-0024510) of the present inventors and refers to coating the surface of a substrate for use in sol-gel biochips with a solution of a high-molecular-weight synthetic coating agent, such as polyvinyl acetate, dissolved in an organic solvent such as methylene chloride or tetrahydrofuran.

As biomaterials which can be immobilized on the biochip according to the present invention, it is possible to use all biomaterials, which can bind specifically to a target substance to allow the binding between them to be analyzed. Preferably, the biomaterials include nucleic acids including DNA, RNA or PNA, proteins and oligopeptides. In addition, it is also possible to immobilize various compounds, including low molecular substances and natural substances.

Non-limiting examples of proteins among biomaterials, which can be integrated on the chip substrate surface at high density according to the present invention, include HIV p24, Combo, RgpIII, HCV core, NS5, NS3, E1/E2, HBV surface antigens and antibodies, IgG-Cy3, antigens or antibodies for infectious disease diagnosis, antigens or antibodies for cancer diagnosis, including AFP (alpha fepto protein), PSA, CA1-1 and glypecan, and enzymes which are used in activity measurement. Also, in addition to proteins, antigens and antibodies, it is possible to immobilize low molecular substances for use in new drug development, and natural substances, including native plants, microorganisms, fungi and herbal medicinal materials, using the sol composition.

According to the present invention, a sol mixture having a composition selected by screening can be spotted on a 96-well plate type substrate without surface treatment, and a biochip having a probe immobilized thereon using the sol mixture can be diagnosed and analyzed using existing automated devices for immune tests without introducing new devices. The analysis process is shown in FIG. 1. As the 96-well plate, any polymer plate commercially available from any manufacturer can be used without particular limitation, but in the present invention, a 96-well plate (NUNC, SPL) was used to immobilize spots and fabricate a chip. Also, as shown in FIG. 1, the automated devices can be used with, for example, Axym (Abott) and a Roche's device.

In the case of a protein chip, the diameter of spots is preferably about 100-500 and 1-1000 spots per well are preferably integrated. In Examples below, a chip having 100 spots/cm$^2$ was fabricated, but it is possible to integrate spots at a high density up to 1,000 spots/cm$^2$.

In the case of a biochip fabricated using a sol-gel reaction in the present invention, reaction results can be obtained within 30 minutes to 2 hours, unlike an immune diagnosis method requiring a long reaction time, or an existing biochip diagnosis method.

The protein chip fabricated according to the present invention can be used in diagnosis by labeling an antigen with a fluorescent dye in the same manner as a sandwich assay as an immune diagnosis method. In this case, in a step of measuring results, the diagnosis results can be analyzed and quantified using a fluorescent scanner through a software program. The protein chip fabricated according to the present invention can substitute for an enzyme immune diagnosis method of HIV, HCV, HBV and the like.

In the inventive sol composition, because biomaterials can be added in a solution state, proteins or low molecular substances can be integrated at high density. Thus, it is possible to perform high throughput screening (HTS) using the fabricated biochip. Also, because enzymes for use in protein activity measurement can be integrated in the sol mixture, the fabricated biochip can be used in the measurement of enzyme activity. The enzymes for activity measurement include enzymes which are used in toxicity analysis, environmental analysis and food bacteria analysis. Thus, the 96-well plate type biochip according to the present invention can be applied for disease diagnosis and can be used not only in fundamental technologies for new drug development, but also in environmental analysis and toxicity analysis.

FIG. 1 shows an analysis method employing the 96-well plate type biochip according to the present invention. In the present invention, a sol composition can be stably immobilized on a 96-well plate without surface treatment, and can be analyzed using an existing immunological diagnostic device in the same manner.

Also, the sol composition according to the present invention can be applied to a prior developed biosensor to increase the sensitivity thereof. The sol composition can be immobilized on polymers, metal surfaces including gold, semiconductor surfaces including silicon, transparent polymer surfaces, glass surfaces including mirror, to increase the sensitivity thereof. To facilitate detection, a target substance is preferably labeled with a signal inducer such as a fluorescent dye. Detection for the binding between biomaterial and the target substance can be performed using various methods, including a fluorescence detection method, an electrochemical detection method, a detection method that uses a change in mass, a detection method that uses a change in electric charge, and a detection method that uses a difference in optical properties, according to the properties of a substrate to which a target substance labeled with a signal inducer is attached.

When the inventive gel composition is used, various kinds of proteins, antigens, antibodies, low molecular substances and bacteria can be integrated in a maximum of 1000 spots per well. The inventive composition can be typically used in blood bank screening for compatibility procedures in blood transfusion (infectious disease markers, for example, HIV I, II, HCV, HBV, malaria, *H. pylori*, Syphillis, etc.) in a blood collection process, and a marker for the diagnosis of general cancer and a marker for the diagnosis of a specific cancer can be integrated on a substrate at the same time and can be used in diagnosis. In addition, according to the present invention, a group of products, including POCT, which can detect diseases and bacteria without a fluorescent label, can be developed using various metal and semiconductor substrates. Also, markers sensitive to environmental pollution, particularly water pollution, can be integrated at the same time, so that water pollution can be detected at once.

EXAMPLE

The present invention will hereinafter be described in further detail by examples. However, it is to be understood that these examples can be modified into other various forms, and the scope of the present invention is not intended to be limited to such examples. Such examples are given to more fully describe the present invention for a person skilled in the art.

Figure 2:
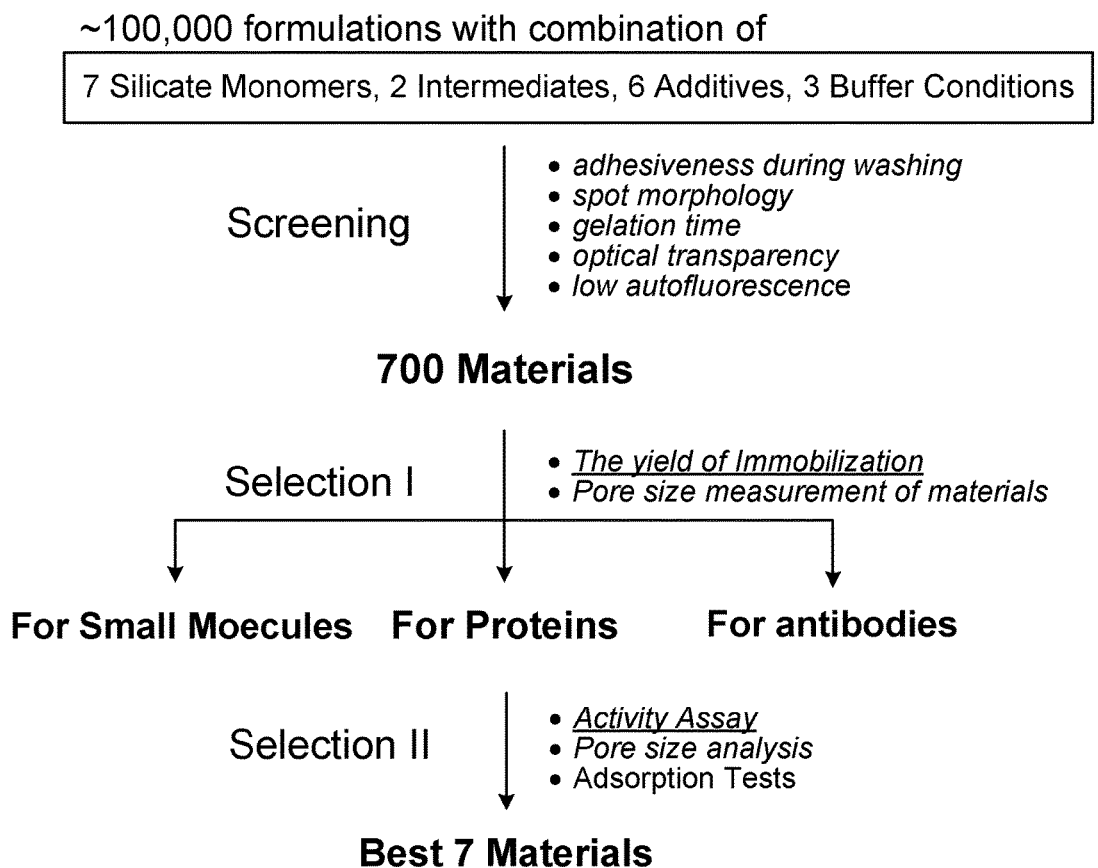
FIG. 2 is a flow diagram showing a method for screening a sol composition which forms spots on a surface-untreated substrate.
Figure 3:
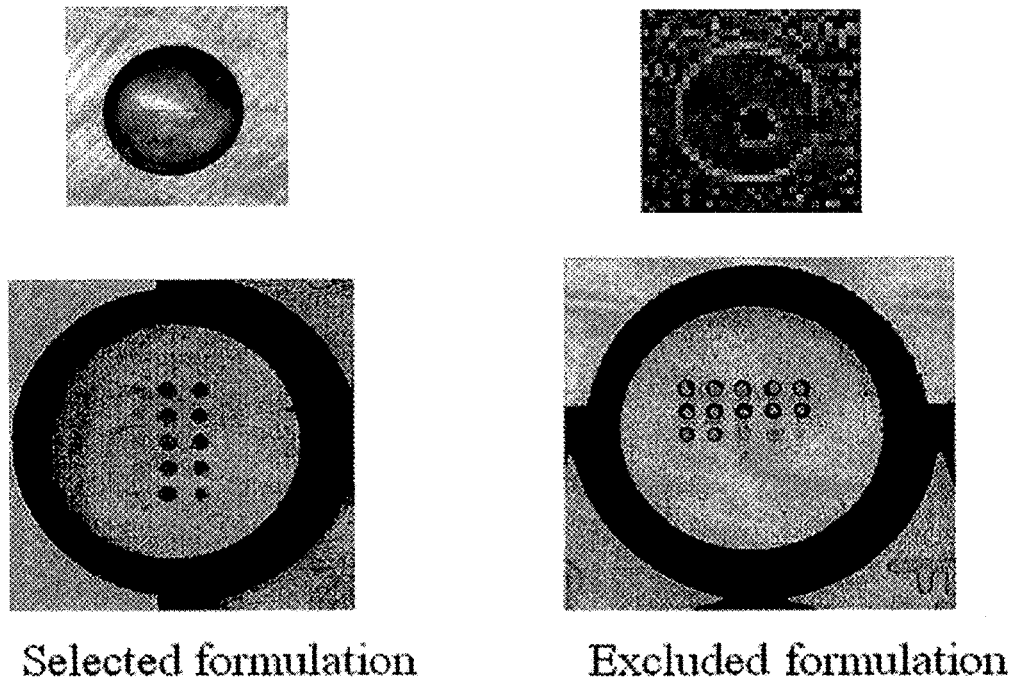
FIG. 3 shows physical properties of protein chip formulation selected from the screening method according to the present invention.

Example 1: Screening of Sol Compositions which are Specific for a Substrate and Biomaterials and, at the Same Time, can be Immobilized Directly on the Substrate A sol-gel composition, which can withstand strong washing even when it is immobilized directly on a surface-untreated substrate, and, at the same time, has excellent physical properties when it is fabricated into a biochip, was rapidly screened by the inventive screening method (FIG. 2). FIG. 2 is a flow diagram showing a method for screening a sol composition which forms spots on a surface-untreated substrate, and FIG. 3 shows examples of compositions selected and excluded in the screening method of FIG. 2. It can be seen that the excluded compositions could not immobilize biomaterials such as proteins without surface treatment and were completely detached during a washing process.

First, about 100,000 sol compositions based on silicate monomers were spotted on a substrate and measured with respect to strong adhesion capable of withstanding washing in an analysis process, physical properties capable of maintaining the shape of spots constant, gelling time, optical transmittance, and low self-fluorescence. From the spotted compositions, a total of 700 compositions were primarily screened, which were not detached even when they were scratched with a tip after washing, had a spot diameter of 100-800 μm while maintaining a circular shape, had a self-fluorescence lower than background fluorescence, and had a gelling time of 4-48 hours in a tube and a gelling time of 1-4 hours in the spots of the substrate.

Among the 700 sol compositions, in view of the immobilization yield of biomaterials and sensitivity in an immune analysis, compositions were selected wherein the immobilization rate of a probe was more than 70% and the ratio of specific signals/non-specific signals of the probe and the target substance was at least 3.

Finally, when biomaterials were low molecular substances, proteins and antibodies, 2 compositions, 7 compositions and 8 compositions, respectively, were obtained.

Hereinafter, the method for screening sol compositions according to the present invention will be described in further detail.

Primary Screening of Sol Compositions

Silicate monomers (TMOS, MTMOS, TEOS, TrEOS, TMS, MTMS 및 3-ATMS), intermediates (PGS and DGS) and additives (GPTMOS, PEOU, glycerol, PEG200, PEG400 and PEG8000) were added to a 10 mM HCl solution to have various compositions. Finally, buffers having different pHs (4-9), concentrations (0-500 mM) and salts (potassium and ammonium) were added to each of the compositions. As a result, more than 100,000 compositions were obtained, and these compositions were integrated on a commercially available PMMA (polymethylmethaacrylate) plate, and tested for adhesion, the appearance of spots, gelling time, transmittance and background.

Adhesion was tested by intense scratching of spots after washing, in which the substrate was intensely washed three times with 1×PBS (containing 10% Tween) at 1200 rpm for 5 minutes, and then spot compositions were selected which were not detached even when they were scratched directly with a tip. The appearance of the spots was observed directly with an optical microscope to select spots, which maintained a circular shape and had a spot diameter of 100-800 μm. Gelling time was measured both in a tube and on the spots, and compositions showing a gelling time of more than 4 hours in the tube and a gelling time of more than 1 hour on the spot were selected. With respect to optical transmittance, compositions determined to have a self-fluorescence lower than background fluorescence using a laser scanner were selected (GenePix 4100, Axon Instrument).

Selection of Optimal Compositions

The spot immobilization rate of each of the primarily screened compositions was measured by comparing the signals of a Cy-3-labeled immobilized peptide, a BSA protein and an antibody before and after a washing process. For activity analysis, a BSA protein (500 ng/μl) was added to each of the primarily screened compositions, and the resulting mixtures were integrated on a PMMA-slide type plate together with the protein. The slide was allowed to react with a Cy-3-labeled BSA antibody (Sigma) for 30 minutes, and then intensely washed with a washing solution (1×PBS, 0.1% Tween (Sigma)), followed by drying. To analyze the sensitivity of signals, the spots of the slide were scanned, and signal value to background value was quantified using the GenePix Pro 4.0 software (Axon Instrument) so as to analyze the sensitivity of signal.

As a result, as shown in Table 1 below, two compositions among the primarily screened compositions showed an immobilization rate of more than 70% for the low molecular substance contained therein, 7 compositions showed an immobilization rate of more than 80% for the protein contained therein, and 8 compositions showed an immobilization rate of about 90% for the antibody.

TABLE 1

Immobilization rate of sol compositions for target substances to be immobilized

| | Immobilization rate (%) | | |
|---|---|---|---|
| | small molecule | protein | antibody |
| Sol compositions for small molecule (2) | 75.5 | 50.5 | 43.2 |
| Sol compositions for protein (7) | 21.1 | 82.7 | 74.5 |
| Sol compositions for antibody (8) | 1.2 | 10.3 | 88.9 |

Surface Analysis

The surface of the spots was observed using SEM (S-4800 SEM, Hitachi Co.). Conductive coating for SEM observation was performed using an ion beam sputter coater with an iridium target (about 20 nm thickness), after the spots were completely gelled. The size of pores was measured using an image analysis software program (Image-Pro Plus, Media-Cybernetics). The number of pores was measured in 9 different areas (576 nm×430 nm), and mean pore density was calculated as [Σ pore area]/[total area (576 nm×430 nm)].

Analysis of Internal Spots in Solution

Internal spot images were measured in air using Tapping-Mode™ AFM (MultiMode SPM, Nanoscope IIIa, Vecco Instrument). The spots were sectioned using a vertical microtome.

Analysis of Spot Scan Profile

Spot images were measured through a standard reflection shape using a con-focal laser scanning microscope (LSM 5 pascal, Carl Zeiss Inc.). The scan profile for the center of the spots was measured to be a thickness of less than 63 μm and a diameter of less than 380 μm.

To measure the distribution of the protein and the antibody in the spots after immune analysis, the vertical tomography image of the internal spots was photographed with CLSM (LSM 5 pascal, Carl Zeiss Inc.). The highest resolution of the z-axis using a stepping motor was 50 nm, and the highest resolutions of the x-axis and y-axis using a scanning module were ×100 and ×40, respectively. To photograph CLSM images, microspots containing a p24 protein were first integrated on a glass slide, the slide having the p24 protein-containing spots integrated thereon was allowed to react with the p24 antibody for 1 hour, and then intensely washed. Then, the slide was allowed to react with a Cy3-labeled secondary antibody for 20 minutes, washed and dried and the CLSM images thereof were photographed.

Measurement of Specificity Between Marker and Target Substance and Activity Thereof To measure the specificity and activity of protein-protein interaction on a sol-gel substrate, a p24 protein as an HIV antigen protein was mixed with the sol composition IV of Table 2 below and immobilized. Immune analysis was performed with serial dilutions of serum containing an HIV antibody corresponding to the p24 protein. At the same time, to confirm the non-specific adsorption of the HIV antibody, a BSA protein was immobilized on the same chip in the sol-gel substrate. Non-specific interaction occurring upon the reaction of a protein (4-1BB) having no connection with the spots of a sol composition containing no protein was very low. However, with the BSA or 4-1BB antibody against BSA or 4-1BB antigen, specific interaction was shown in exact spots.

Table 2 shows the properties of 7 sol compositions for protein immobilization, screened by the present invention. In Table 2, composition 0 is a comparative composition consisting only of TMOS and MTMS.

Among said 7 compositions for protein immobilization, compositions IV showed the best results with respect to signals and signal/background ratio. The composition IV had low TMOS ratio compared to the other compositions, contained high-molecular weight PEG, and showed high pore density and low non-specific antibody content.

TABLE 2

Analysis of properties of compositions for protein immobilization

| Sol compositions | Composition | Activity | Pore properties of spot size (nm) | density | Adsorption ability |
|---|---|---|---|---|---|
| 0 | 25.5% TMOS, 12.5% MTMS | 1.1475 | 12.4 | 0.07 | 1993.33 |
| I | 17.5% TMOS, 12.5% MTMS 4% PGS | 3.45084 | 21.9 | 0.188 | 578.29 |

TABLE 2-continued

Analysis of properties of compositions for protein immobilization

| Sol compositions | Composition | Activity | Pore properties of spot size (nm) | density | Adsorption ability |
|---|---|---|---|---|---|
| II | 20.5% TMOS, 10.5% MTMS 5% PEOU | 6.35116 | 21.3 | 0.102 | 304.06 |
| III | 25.5% TMOS, 12.5% MTMS 3% PEG400 | 18.8969 | 27.8 | 0.349 | 265.66 |
| IV | 25.5% TMOS, 12.5% MTMS 5% PEG8000 | 37.43029 | 21.5 | 0.259 | 14.69 |
| V | 25.5% TMOS, 12.5% MTMS 2.5% glycerol | 16.58053 | 21.9 | 0.139 | 77.24 |
| VI | 25.0% TMOS, 7.5% MTMS 5% GPTMOS | 3.45084 | 17.6 | 0.053 | 517.62 |
| VII | 10% MTMS | 5.3421 | 20.4 | 0.119 | 99.64 |

Example 2: Enzyme Immunological Diagnosis of Disease Through Immobilization of Sol-Gel Protein Chip Spots Immobilized on 96-Well Plate In this Example, the sol compositions selected in Example 1 were measured using an automated ELISA diagnosis process which is currently used for hepatitis diagnosis. The automated diagnosis process comprised an intense washing process, and thus among the screened compositions, a composition was used in which the spots showed strong adhesion and could maintain the characteristic circular shape thereof even after washing. The sol composition used in this Example was optimized such that the formed spots could withstand even physical scratching using Abbott Axsym and a Roche Elecsys device.

In this Example, when the material of a 96-well plate for the composition selected through this process was plasma-treated PMMA, a mixture of the sol composition for immobilization and a protein solution consisted of 17.5-25 parts by weight of TMOS, 5-15 parts by weight of MTMS, 2.5-15 parts by weight of GPTMOS, 12.5 parts by weight of 10 mM HCl, 25 parts by weight of distilled water, 12.5 parts by weight of 10 mM sodium phosphate buffer (pH 5.8) and 12.5 parts by weight of a protein solution.

In the case of compositions containing TMOS in an amount larger than the upper limit of the range of 17.5-25 parts by weight, the immobilization rate of the target substance was low, due to excessively low pore density and small pore size, and in the case of compositions containing TMOS in an amount smaller than the lower limit of said range, the target substance was not immobilized due to excessively high pore density and large pore size. In the case of compositions containing MTMS in an amount larger than the upper limit of the range of 5-15 parts by weight, the immobilization rate of the target substance was low, due to excessively low pore density and small pore size, and the case of compositions containing MTMS in an amount lower than the lower limit of said range, the target substance was not immobilized due to excessively high pore density and large pore size. In the case of compositions containing GPTMOS in an amount larger than the upper limit of the range of 2.5-15 parts by weight, a lot of nonspecific reactions occurred due to high adsorption ability of the spots, and the case of compositions containing GPTMOS in an amount smaller than the lower limit of said range, the target substance was not easily immobilized due to large pore size.

Figure 4:
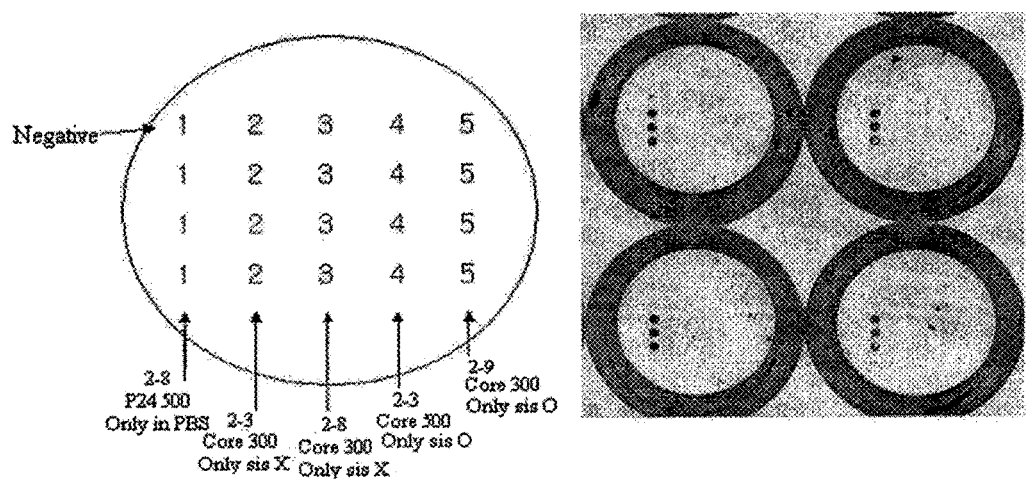
FIG. 4 shows HIV diagnosis results obtained by mixing HIV antigen protein p24 with the sol composition obtained through the inventive screening process, immobilizing the antigen protein on a 96-well plate without surface treatment and performing the diagnosis of an HIV patient using the immobilized antigen.

Using HIV antigen, p24 protein as a protein solution, sol-gel spots were integrated on a 96-well plate. As a result, as shown in FIG. 4, four samples showed a reaction specific for the HIV p24 protein, indicating that the samples were all HIV-positive. The protein could be strongly three-dimensionally immobilized on the 96-well plate made of plasma-treated PMMA using the sol-gel mixture, and the results of antigen-antibody reactions could be confirmed using the biochip through the existing automated diagnosis device and an assay method.

Also, a mixture of a sol composition and a protein solution, for immobilization on a 96-well plate made of plasma-untreated commercial PMMA, was composed of 22.5-25 parts by weight of TMOS, 7.5-10 parts by weight of MTMS, 2.5-5 parts by weight of GPTMOS, 12.5 parts by weight of 10 mM HCl, 25 parts by weight of distilled water, 12.5 parts by weight of 10 mM sodium phosphate buffer (pH 5.8), and 12.5 parts by weight of a protein solution.

In the case of compositions containing TMOS in an amount larger than the upper limit of the range of 22.5-25 parts by weight, the immobilization rate of the target substance was low, due to excessively low pore density and small pore size, and in the case of compositions containing TMOS in an amount smaller than the lower limit of said range, the target substance was not immobilized due to excessively high pore density and large pore size. In the case of compositions containing MTMS in an amount larger than the upper limit of the range of 7.5-10 parts by weight, the immobilization rate of the target substance was low, due to excessively low pore density and small pore size, and the case of compositions containing MTMS in an amount lower than the lower limit of said range, the target substance was not immobilized due to excessively high pore density and large pore size. In the case of compositions containing GPTMOS in an amount larger than the upper limit of the range of 2.5-5 parts by weight, a lot of nonspecific reactions occurred due to high adsorption ability of the spots, and the case of compositions containing GPTMOS in an amount smaller than the lower limit of said range, the target substance was not easily immobilized due to large pore size.

Figure 5:
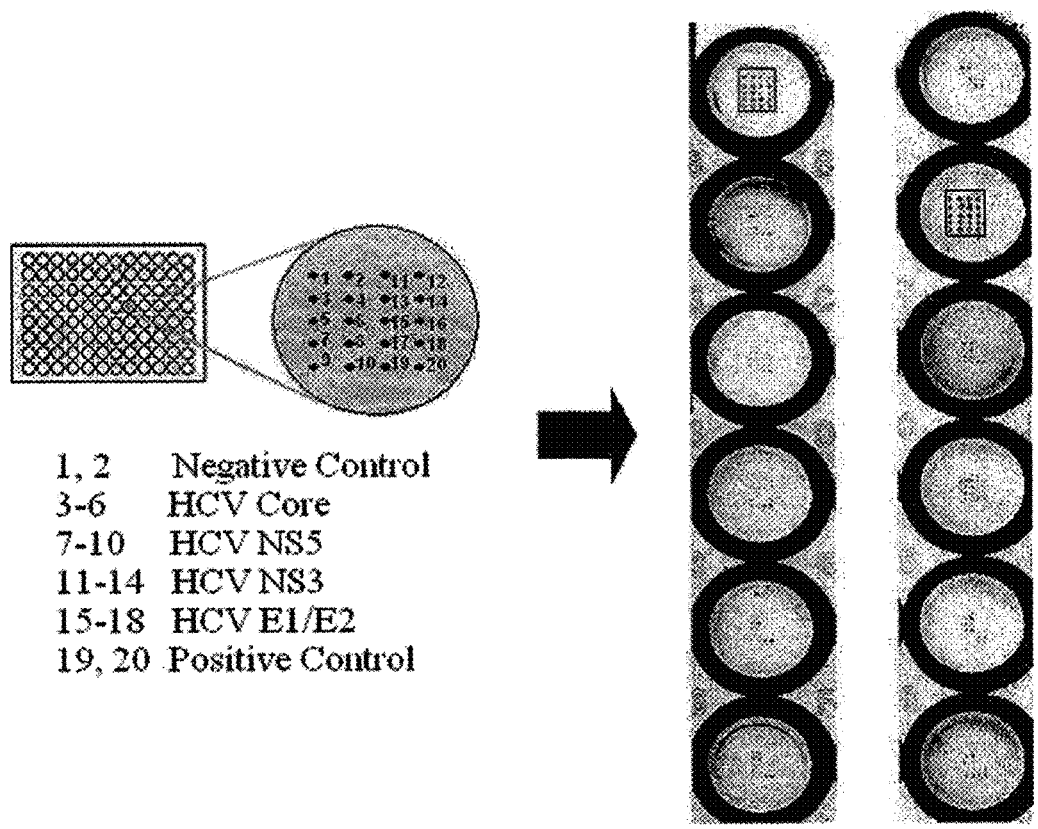
FIG. 5 shows HCV diagnosis results obtained by mixing an HCV marker with the sol composition obtained through the inventive screening process, immobilizing the marker on a 96-well plate without surface treatment and performing the diagnosis of hepatitis C using the immobilized marker.

The optimized composition was mixed with an HCV antigen and integrated on a 96-well plate made of plasma-untreated PMMA, thus preparing a biochip. Using the biochip, a test was performed on 79 patients (negative: 25 persons, and positive: 54 persons) with the Roche HCV EIA kit. FIG. 5 shows blood analysis results for 12 patients. As can be seen in FIG. 5, the test results obtained using the biochip were completely consistent with the test results obtained using the existing ELISA method, suggesting that the inventive biochip had high reproducibility of results. The biochip according to the present invention had high performance, high sensitivity, high throughput and high accuracy, and could perform measurements at low cost, suggesting that it would substitute for existing ELISA diagnosis methods. Also, the inventive biochip could immobilize the protein in an amount larger than that in the existing immune diagnosis method, so that the false positives thereof could be reduced compared to the existing diagnosis method, and thus more accurate hepatitis diagnosis could be performed.

Figure 6:
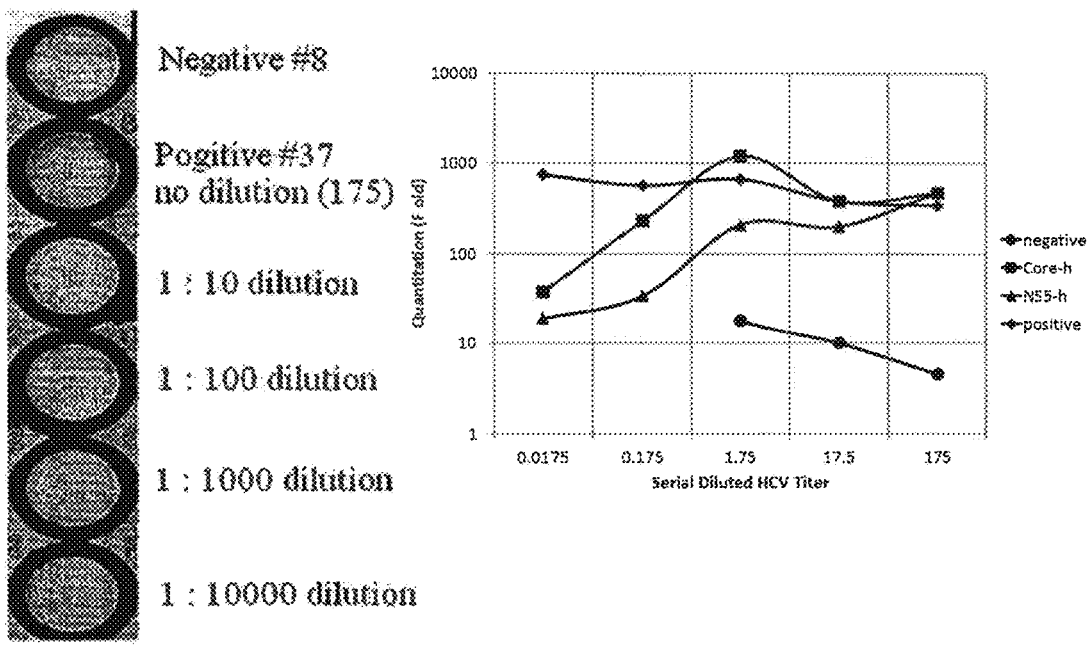
FIG. 6 shows detection limit (sensitivity) for sol-gel protein chip according to the present invention. Left is the results of hepatitis C diagnosis performed using a biochip having a sol composition according to the present invention immobilized thereon and Right is a graphic diagram showing results obtained by quantitatively analyzing the diagnosis results using a quantification software program.

Also, in order to examine whether quantitative analysis can be performed using the inventive biochip, tests on detection limits and quantification ranges were performed through serial dilutions of patient samples (FIG. 6). As a result, quantitative distribution was shown. From the test results, it could be seen that, when the biochip according to the present invention was used, quantitative analysis, which could not be performed in existing immune diagnosis methods, could also be performed.

Example 3: Fabrication and Analysis of Biochip Using Gold Chip Substrate

In this Example, a sol composition for immobilization on a gold chip substrate was selected according to the same method as in Example 1 using a gold (Au) chip used in a SPRi system. In the case of the gold chip, adhesives (1010 and 1020; LG Chemical Co., Ltd., Korea) as additives were added to the sol composition for immobilization. The sol mixture after spotting was modified into a substance, which was transparent like glass and had pores, but the sol mixture was not immobilized on the gold chip, the surface of which was coated with Au. In this Example, in order to immobilize sol spots on the gold chip surface, additives were used, and the composition of the used sol mixture was composed of 16.2-18.7 parts by weight of TMOS, 3.7-6.2 parts by weight of MTMS, 13.7-16.2 parts by weight of GPTMOS, 0.01-20 parts by weight of adhesives (1010, 1020, etc.), 12.5 parts by weight of 10 mM HCl, 23.7-24.5 parts by weight of distilled water, 12.5 parts by weight of 10 mM sodium phosphate buffer (pH 5.8), and 12.5 parts by weight of a protein solution.

In the case of compositions containing TMOS in an amount larger than the upper limit of the range of 16.2-18.7 parts by weight, the immobilization rate of the target substance was low, due to excessively low pore density and small pore size, and in the case of compositions containing TMOS in an amount smaller than the lower limit of said range, the target substance was not immobilized due to excessively high pore density and large pore size. In the case of compositions containing MTMS in an amount larger than the upper limit of the range of 3.7-6.2 parts by weight, the immobilization rate of the target substance was low, due to excessively low pore density and small pore size, and the case of compositions containing MTMS in an amount lower than the lower limit of said range, the target substance was not immobilized due to excessively high pore density and large pore size. In the case of compositions containing GPTMOS in an amount larger than the upper limit of the range of 13.7-16.2 parts by weight, a lot of nonspecific reactions occurred due to high adsorption ability of the spots, and the case of compositions containing GPTMOS in an amount smaller than the lower limit of said range, the target substance was not easily immobilized due to large pore size.

Figure 7:
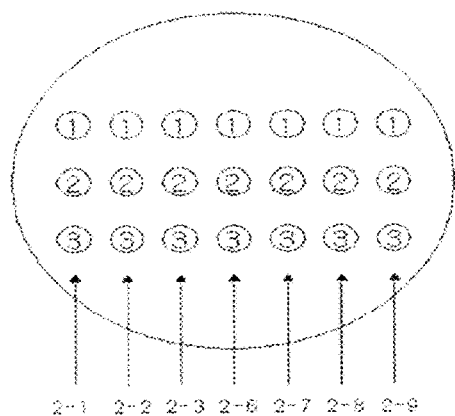
FIG. 7 shows a gold chip fabricated by spotting a sol composition screened according to the inventive method on gold (Au) substrate.
Figure 7:
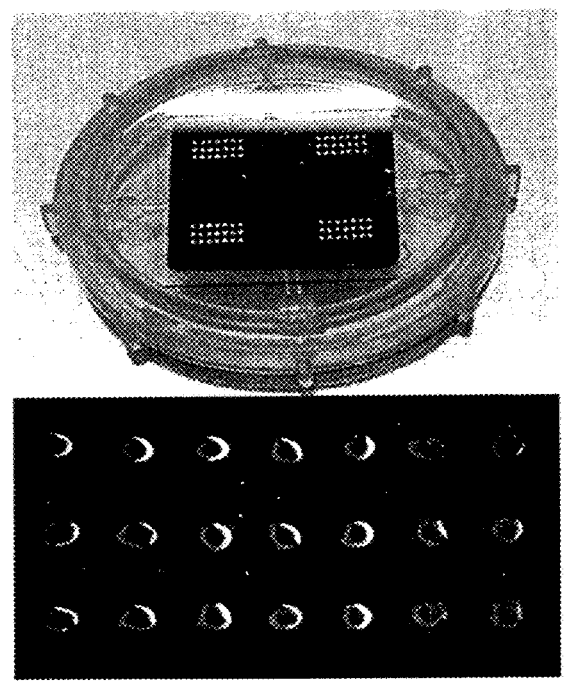

The mixture was spotted on the gold chip in the same manner as in Examples 2 and 3, and then assayed for a p24 protein. The difference of the gold chip assay from the assay of the biochip immobilized on the 96-well plate was that a primary antibody reaction was performed and results could be detected without a fluorescence-labeled secondary reaction. The results of the gold chip subjected to the primary reaction could be read by measuring and imaging a change in resonance occurring during the reaction, using the SPR system (FIG. 7). The gold chip could immobilize a large amount of protein and detect protein-protein binding directly without chemical labeling, and thus it had high sensitivity.

Example 4: Immobilization and Electrochemical Detection of Spots on Semiconductor Chip This Example relates to a system in which a conductive sol mixture was immobilized on the positive electrode of a semiconductor chip for use in electrochemical measurements, and the difference in electrical resistance before and after a reaction occurring therebetween was measured to monitor the reaction. A metal surface used in this Example was a silicon wafer most frequently used in electrodes, but it was difficult in the prior art to attach a polymer substance to the silicon wafer without surface treatment, because the surface thereof was very uniform and smooth. However, in this Example, a sol composition for immobilization on electrodes was screened according to the method of Example 1 and mixed with protein p24, and the mixture was immobilized on a semiconductor wafer.

The sol composition for semiconductor chips, used in this Example, was composed of 5-30 parts by weight of TMOS, 2-35 parts by weight of MTMS, 1-15 parts by weight of GPTMOS, 0.01-20 parts by weight of adhesives, 12.5 parts by weight of 10 mM HCl, 23.7-24.5 parts by weight of distilled water, 12.5 parts by weight of 10 mM sodium phosphate buffer (pH 5.8), and 12.5 parts by weight of a probe solution.

Figure 8:
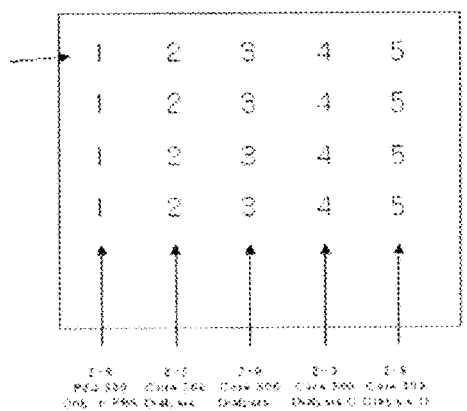
FIG. 8 is a semiconductor chip fabricated by spotting a sol composition screened according to the inventive method on a semiconductor substrate.
Figure 8:
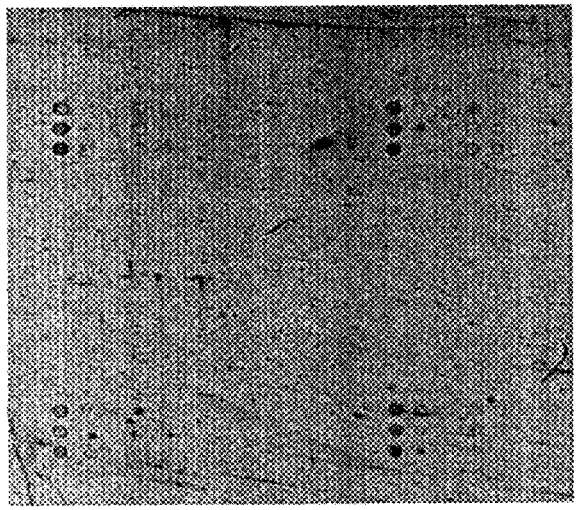

Using the semiconductor chip on which the sol composition and the protein p24 were immobilized, the difference in electrical resistance before and after a reaction was measured according to an electrochemical measurement method, and the measurement results are shown in FIG. 8. As shown in FIG. 8, sensitivity was significantly increased, and background to noise ratio could be reduced. Thus, the semiconductor chip according to this Example is inexpensive and, at the same time, is useful for the fabrication of small-sized biochip analysis systems.

INDUSTRIAL APPLICABILITY

As described above in detail, the present invention provides the method for screening a sol composition for sol-gel biochips, which is used to immobilize a probe on a surface-untreated substrate. Also, the present invention provides a sol composition for PMMA substrates, gold chip substrates and silicon wafer substrates, screened by said method, and a sol-gel biochip prepared using said sol composition. The biochip according to the present invention is convenient and economical, because it can employ existing reaction systems and analysis systems by immobilizing biomaterial-containing gel type spots directly on 96-well plates, which are widely used in bioassays. Also, the biochip can provide good analysis results, because less modification of biomaterials immobilized on the biochip occurs. In particular, when the biochip is used in an analysis method without a probe in addition to fluorescence analysis, the sensitivity problem occurring in the prior analysis method can be solved by strongly binding three-dimensional sol-gel spots, and thus the biochip is expected to be useful for the development of products, including POCT.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A method for screening a sol composition for sol-gel biochips, which is used to immobilize a probe on a surface-untreated substrate, the method comprising the steps of:
   (a) obtaining a first library of sol compositions wherein at least one silicate monomer selected from the group consisting of tetramethylorthosilicate (TMOS), methyltrimethoxysilane (MTMOS), tetraethylorthosilicate (TEOS), ethyltrimethoxysilane (ETrEOS), trimethoxysilane (TMS), methyltrimethoxysilicate (MTMS) and 3-aminopropyltrimethoxysilicate (3-ATMS), and at least one additive selected from the group consisting of polyglyceryl silicate (PGS), diglyceryl silane (DGS), 3-glycidoxypropyl trimethoxysilane (GPTMOS), (N-triethoxysilylpropyl)-0-polyethylene oxide urethane (PEOU), glycerol and polyethylene glycol (PEG) having a molecular weight of 100-10,000, are mixed with each other in buffer at various ratios;
   (b) spotting the first library of sol compositions on a surface-untreated target substrate;
   (c) measuring the adhesion, appearance, transmittance and gelling time of the spots formed in the step (b), and selecting, based on the measurement results, compositions, which do not show the detachment of spots even when they are scratched with a tip after washing, have a spot diameter of 100-800 μm while maintaining a circular shape, show a self-fluorescence lower than background fluorescence, and have a gelling time of 4-48 hours in a tube and a gelling time of 1-4 hours on the spots of the substrate, thereby obtaining a second library of sol com positions;
   (d) adding a probe to the second library of sol compositions and spotting the probe-containing second library on a surface-untreated substrate; and
   (e) measuring the immobilization rate of the spots for the probe, and the specificity between the probe and a target substance, and selecting, based on the measurement results, a sol composition wherein the immobilization rate of the probe is at least 70% and the ratio of specific signals/non-specific signals of the probe and the target substance is at least 3.

2. The method for screening a sol composition for sol-gel biochips according to claim 1, wherein the probe is any one selected from the group consisting of proteins, oligopeptides, nucleic acids, low molecular substances, microorganisms, fungi and herbal medicinal materials.

3. The method for screening a sol composition for sol-gel biochips according to claim 1, wherein the surface-untreated substrate is any one selected from the group consisting of polymer plates, metals, silicon wafers, glass and LCD.

4. A sol composition for sol-gel biochips, which is used to immobilize a probe on a surface-untreated gold substrate, the sol composition comprises:
   16.2-18.7 parts by weight of TMOS;
   3.7-6.2 parts by weight of MTMS;
   13.7-16.2 parts by weight of GPTMOS;
   0.01-20 parts by weight of an adhesive;
   12.5 parts by weight of 10 mM HCl;
   23.7-24.5 parts by weight of distilled water;
   11-13 parts by weight of 10 mM sodiumphosphate buffer (pH 5.8); and
   10-15 parts by weight of a probe solution.

5. The sol composition for sol-gel biochips according to claim 4, wherein said probe is protein.

6. A sol-gel biochip, in which the sol composition of claim 4 is immobilized on a surface-untreated gold substrate.

7. A sol composition for sol-gel biochips, which is used to immobilize a probe on a surface-untreated silicon substrate, the sol composition comprises:
   5-30 parts by weight of TMOS;
   2-35 parts by weight of MTMS;
   1-15 parts by weight of GPTM OS;
   0.01-20 parts by weight of an adhesive;
   12.5 parts by weight of 10 mM HCl;
   23.7-24.5 parts by weight of distilled water;

12.5 parts by weight of 10 mM sodium phosphate buffer (pH 5.8); and 12.5 parts by weight of a probe solution.

8. The sol composition for sol-gel biochips according to claim 7, wherein said probe is protein.

9. A sol-gel biochip, in which the sol composition of claim 7 is immobilized on a surface-untreated silicon substrate.

* * * * *